United States Patent
Tse (12)

(10) Patent No.: US 10,136,699 B1
(45) Date of Patent: Nov. 27, 2018

(54) MASSAGING INSOLE FOR FOOTWEAR WITH MECHANIC AND MAGNETIC ENERGY

(71) Applicant: Crystal K Tse, Rowland Heights, CA (US)

(72) Inventor: Crystal K Tse, Rowland Heights, CA (US)

( * ) Notice: Subject to any disclaimer, the term of this patent is extended or adjusted under 35 U.S.C. 154(b) by 0 days.

(21) Appl. No.: 15/649,540

(22) Filed: Jul. 13, 2017

(51) Int. Cl.
| | |
|---|---|
| A43B 7/14 | (2006.01) |
| A43B 17/00 | (2006.01) |
| A43B 17/02 | (2006.01) |
| A43B 1/00 | (2006.01) |
| A61N 2/06 | (2006.01) |

(52) U.S. Cl.
CPC ............ A43B 7/146 (2013.01); A43B 1/0054 (2013.01); A43B 7/141 (2013.01); A43B 17/006 (2013.01); A43B 17/026 (2013.01); A61N 2/06 (2013.01)

(58) Field of Classification Search
CPC ....... A43B 7/146; A43B 7/141; A43B 1/0054; A43B 17/006; A43B 17/026
USPC .......................................................... 36/141
See application file for complete search history.

(56) References Cited

U.S. PATENT DOCUMENTS

| | | | | |
|---|---|---|---|---|
| 6,405,456 | B1 * | 6/2002 | Nichelson | A43B 1/0054 36/27 |
| 7,200,956 | B1 * | 4/2007 | Kotha | A43B 1/0054 36/1 |
| 2003/0009910 | A1 * | 1/2003 | Pavone | A43B 1/0054 36/29 |
| 2004/0154190 | A1 * | 8/2004 | Munster | A43B 1/0054 36/28 |
| 2016/0235160 | A1 * | 8/2016 | Lam | A43B 17/026 |

FOREIGN PATENT DOCUMENTS

| | | | |
|---|---|---|---|
| JP | 11155606 A | * | 6/1999 |
| JP | 2000079002 A | * | 3/2000 |

* cited by examiner

*Primary Examiner* — Ted Kavanaugh (57) ABSTRACT

An insole for footwear with a built in hydraulic system and magnet that allows for better balance to help avoid falling, better weight distribution, improved massage effect and pain relief. The insole includes a topfoil and bottomfoil which are welded together along their respective edge areas to form a fluid-tight bladder with a fore foot reservoir, flow control means and a rear foot reservoir.

3 Claims, 8 Drawing Sheets

MASSAGING INSOLE FOR FOOTWEAR WITH MECHANIC AND MAGNETIC ENERGY

BACKGROUND OF THE INVENTION

Fluid filled insoles have long been known in the art, U.S. Pat. No. 4,567,677 to James Zona, Allison Park, U.S. Pat. No. 5,978,086 to Soeren Vindrils and U.S. Pat. No. 6,178,663 to Henning R. Schoesler. They substantially work with controlling the fluid flow back and forth to cushion the shocks for pressure and pain relief with just the flow only, the massaging effects are minimal. U.S. Pat. No. 8,857,076 to Elizabeth Langvin et. al provides good shock absorption, but the invention is complicated and costly to make. Additionally, U.S. Pat. No. 8,857,076 to Elizabeth Langvin et. al requires many components like internal pump, motors and valves which lend to the complicated manufacturing process and increased manufacturing costs. The increase in manufacturing costs may transfer to the consumer in the form of a higher selling price which will be disadvantageous to the consumer in an economical manner.

BRIEF SUMMARY OF THE INVENTION

Balance, gait and other coordinated movements of humans and other mammals rely on the real-time control of muscle contractions in response to volition and changes in the environment. This muscular control is coordinated by the central nervous system (CNS), i.e. the brain and spinal cord, but is reliant on sensory feedback from the extremities. Of preliminary importance are the mechanical senses that convey knowledge of skin contact with the environment and limb position.

Lack of adequate mechanical sensory feedback is strongly correlated to significant health problems in humans. These include, for example, the tendency of elderly individuals to fall and the occurrence of skin ulceration (open wounds) of the skin of the feet in people suffering from diabetes.

A collection of specialized sensory cells, called mechanoreceptors, is responsible for providing this flow of sensory information from the extremities. Mechanoreceptors transduce mechanical stimuli from the body's movements and interactions with the environment into electrical signals that can be transmitted and interpreted by the central nervous system. Mechanoreceptors of various types, and found in various anatomic structures, have been identified by researchers in this field. For example, Pacinian corpuscles and other related sensory neurons, found in the skin and deeper subcutaneous layers, are sensitive to touch, stretch, pressure, and vibration ("tactile sense"). Other types of mechanoreceptors may provide muscle information about muscle force, muscle strength, and joint angles ("joint sense" or "proprioception").

Many health conditions and diseases (e.g. aging, diabetes, stroke, neuropathies, trauma and injury, etc.) can negatively impact either the sensitivity of the mechanoreceptors themselves, the transmission of nerve impulses (action potentials on axons), or the interpretation of nerve impulses centrally at the level of the spine or brain.

It is possible to improve the sensitivity of mechanoreceptors using particular forms of mechanical and magnetic energy stimulation applied to the tissues in which the mechanoreceptors are found. Magnetotherapy uses magnetic fields to provide therapeutic and restorative treatments to limbs, organs, and other parts of the body. Generally, one means by which magnetotherapy may be achieved is by bringing a magnet into close proximity to an affected body part.

Mechanical stimulation applied to the tissues further stimulates an increase in blood circulation, which may improve the sensitivity of mechanoreceptors. As with various forms of occupational therapy, injured individuals often seek professional massages to rehabilitate their muscles. The act of physically applying pressure to strategic pressure points located on the human anatomy has been shown to bring relief from pain and reduce fatigue. With a disc, which may also exist as a magnet, the solid projection is able to massage the sole of the foot as the user walks. This constant massaging action may to generate some of the same benefits as the professional therapist, such as pain relief and a reduction in fatigue.

It is an object of the present invention to provide new and improved items of footwear which have improved shock absorbing properties and which provide massaging effects, lift and propulsion, stimulation of the nerves, and better blood circulation to the foot of a wearer when standing, walking or running.

As a user walks, the user's weight is initially applied to the heel of the rear reservoir, and then is transferred to the ball of the foot of the front reservoir. This causes the fluid within the bladder to move, respectively, from the hindfoot region (rear reservoir) to the forefoot region (front reservoir) and then back towards the hindfoot again with means for controlling and restricting the rate of fluid flow vis-à-vis viscosity and density of the fluid, the foot will not simply "jump through" the fluid in the insole when the wearer's weight is applied, and thus the fluid insole has greater pressure distribution.

The reservoirs, front reservoir and rear reservoir, are filled with a large molecular, non-evaporable, highly viscous, sterile liquid. I refer to this as a "heavy liquid." For the above reasons, the density of the fluid, measured by g/cm3, is higher than the density of water (density=weight), because a higher weight of the fluid (compared to water) restricts the flow of the fluid. For the same reasons, the thickness (viscosity) is also higher than water, because a higher thickness of the fluid (compared to water) restricts the flow of fluid. This mixture is sterile, non-toxic and resistant to contamination by bacteria or other microorganisms, thereby ensuring an environmentally safe fluid within the insole.

A number of advantages are achieved by positioning a high gauss permanent magnet in the middle of medial side arch.

The insole is a system for harvesting the user's mechanical energy from moving or walking. The energy may be in a form of movement which involves a compression and decompression of reservoirs situated in the footwear. There may be a back reservoir in the heel area and a front reservoir in the toe area of the footwear. The reservoirs may be filled with fluid that moves in and out upon compression and depression of the reservoir at the heel and toe areas upon the ambulatory motion of a person wearing the footwear. Thus creating lift and propulsion that may cause the permanent magnet to go up and down which may apply neurological stimulation to the soles of the feet.

A hydraulic system incorporates human bipedal motion that converts ambulatory motion into mechanical energy with the combination of magnetic energy of the permanent magnet to achieve the optimal benefits to stimulate the neurosensory of the foot for therapeutic purposes, such as improving blood flow. A person having ordinary skill in the art will recognize that the term permanent magnet is a material exhibiting a persistent magnetic field even without its application of external energy.

The shock absorbing aspect of this invention may be used in any type of footwear, such as sports/athletic shoes, boots, casual shoes, work shoes, children's shoes, orthopedic shoes, sandals and the like. It will significantly reduce shock to the body while walking, running or in other types of foot motion, and will add lift and propulsion, thereby reducing fatigue.

The density and viscosity of the fluid inside the reservoirs (front reservoir and rear reservoir) generally controls the rate of flow of the viscous liquid within the insole. In this way, the density and viscosity determine not only the degree of pressure distribution with following reduction of peak pressures on the plantar surface of the foot, but also directional stability. The liquid used is a thick or heavy liquid that is resistant to flow, but not so thick that flow is unduly restricted. It is intended that when body weight is applied to one area of the reservoir, the fluid will slowly and gradually flow out of the area, thus the fluid is functioning as a flow restricting means and thereby enable an improved weight pressure distribution as compared to the fluid being ordinary water.

The present invention also pertains to energy converters, and particularly to the capture and conversion of bodily motion to a form of energy.

The present invention provides a method and wearable system for enhancing human balance and gait and preventing foot injury through neurological stimulation of the foot.

It is therefore an object of the present invention to provide a new massaging shoe device apparatus and method which has many of the advantages of the massaging shoe devices mentioned heretofore and many novel features that result in a new massaging shoe device which is not anticipated, rendered obvious, suggested, or even implied by any of the prior art massaging shoe devices, either alone or in any combination thereof.

It is another object of the present invention to provide a new massaging shoe device, which may be easily and efficiently manufactured and marketed. An even further object of the present invention is to provide a new massaging shoe device which is susceptible to a low cost of manufacturing with regard to both materials and labor, and which accordingly is then susceptible to low prices of sale to the consuming public, thereby making such massaging shoe device economically available to the buying public.

In view of the above, it is a general purpose of this invention and its various embodiments, which will be described in greater detail, to provide methods and apparatuses to present forms of non-invasive stimulation to the surface of the skin as a means to improve or otherwise enhance mechanoreceptor performance. Further, it is a general purpose of this invention to serve as a therapy for individuals with degraded sensory performance. Still further, it is an additional purpose of the present invention to provide a massage therapy to improve blood flow to prevent or alleviate skin ulceration and the like.

The insole of the invention has been tested and found to provide several desirable medical and therapeutic benefits. The insole relieves fatigue during prolonged standing or walking by distributing the user's weight evenly and symmetrically over the area of the foot, thereby reducing peak pressures exerted on the plantar surface of the user's foot and the deformation of soft tissue. The reduction in pressure thereby further relieves stress on the bones of the foot that can cause foot pain, hard skin and in extreme situations, ulceration.

Importantly, the invention and its various embodiments can be useful in those instances in which augmenting normal mechanoreceptor performance can compensate in part for problems of axonal transmission and CNS interpretation of sensory information. Similarly, enhancing the sensitivity of mechanoreceptors can be useful in improving overall sensorimotor performance in individuals with no neurological deficits.

The present invention advantageously provides novel methods and apparatuses for improving balance and gait by applying neurological stimulation to the soles. It is further an object of the present invention to provide novel methods and apparatuses for reducing the likelihood of injuries to the foot, especially in individuals suffering from diabetic or other neuropathies, by applying neurological stimulation to the soles of the feet.

It is further an object of the present invention to provide novel methods and apparatuses for improving general sensorimotor performance, including that required in normal or athletic activity, by applying neurological stimulation to the soles and other surfaces of the feet.

It is further an object of the present invention to provide novel methods and apparatuses for improving balance, gait, and general sensorimotor performance and for reducing the likelihood of injuries to the foot by applying neurological stimulation to tendons, ligaments, and muscles.

The controlled flow of the heavy fluid, previously mentioned, through the bladder across the plantar surface of the user's feet provides a therapeutic movement of the small intrinsic muscles of the feet. The movement of the muscles stimulates the venous pump function to increase blood circulation, which in turn improves the transport of oxygen and nutrients to the cells in the foot and the removal of waste products excreted from the cells. Improved blood circulation reduces the amount of lactic acid, thereby reducing the occurrence of tired muscles.

Another aspect of the present invention is that the neurological stimulation be imparted either mechanically or magnetically or both to the soles and other surfaces of the feet and/or to the ankle.

DETAILED DESCRIPTION OF THE INVENTION

FIGS. 1 through 5 and FIGS. 8 through 9 illustrate a first embodiment of the fluid filled insole of the invention. The insole comprises an upper layer 11 and a lower layer 12 with four regions namely rear reservoir 1, flow control passageways 2, 2a, and 2b, front reservoir 3 and distal front 4. The upper layer 11 and lower layer 12 are made out of flexible material and are sealed together at their peripheral margins 6. Said upper layer 11 and said lower layer 12 are sandwiching a fluid filled reservoir. The cavity between upper layer 11 and lower layer 12 comprises two main regions, namely a rear reservoir 1, a front reservoir 3. Between rear reservoir 1 and front reservoir 3 are at least three narrowed passageways 2, 2a and 2b. For reference, the medial passageway is numbered 2a and the lateral passageway is numbered 2b.

The cavity of rear reservoir 1 and front reservoir 3 are filled with a heavy and viscous fluid that has a density, measured by g/cm3, higher than the density of ordinary water. The said fluid may flow between and through the rear reservoir 1, front reservoir 3 and passageways 2, 2a and 2b. The distal front foot 4 preferably does not contain fluid. The distal front foot 4 comprises a upper layer 11 and lower layer 12 which are sealed together.

Along passageways 2, 2a and 2b there are at least two curved welded seams 7 and 8. Seam 7 is curved inwards medially with a magnet 5 sealed inside. Seam 8 is curved outward laterally. Within the front reservoir 3 region there are at least three transversely spaced welded seams 9, 9a and 9b. The welded seams 7 and 8 form medial passageway 2a and lateral passageway 2b. Passageways 2, 2a and 2b are able to act as flow regulators where heavy and viscous fluid may flow through. The narrowing of the passage between rear reservoir 1 and front reservoir 3 due to passageways 2, 2a and 2b allow for said passageways to act as a means for fluid restriction and thus, fluid regulators.

The welded seams 7, 8, 9, 9a and 9b are formed by joining the upper layer 11 to the lower layer 12.

Figure 2:
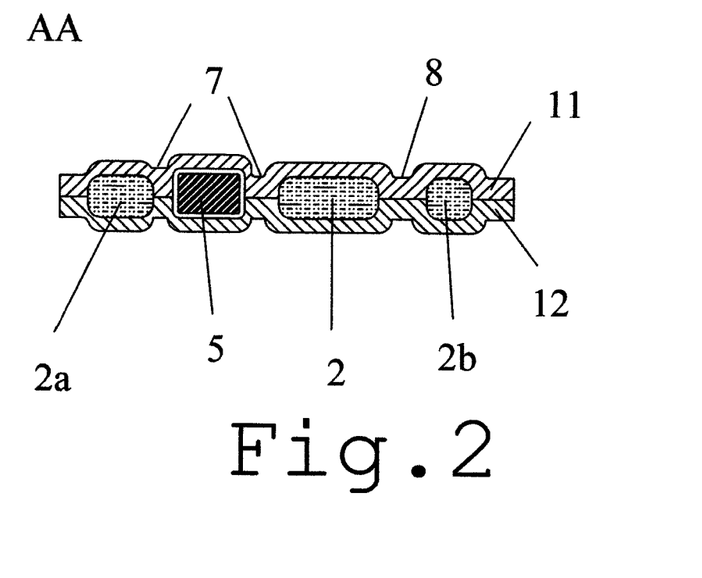
FIG. 2 is a cross section AA.

FIG. 2 shows a cross section AA through the first embodiment fluid filled insole. The passageways 2, 2a and 2b are organized transversely. A magnet 5 is sandwiched between upper layer 11 and lower layer 12. The magnet 5 is disposed along welded seam 7 and between medial passageway 2a and central passageway 2. A heavy and viscous fluid may flow through passageways 2, 2a and 2b whereas fluid may not be in reach of the magnet 5.

Figure 3:
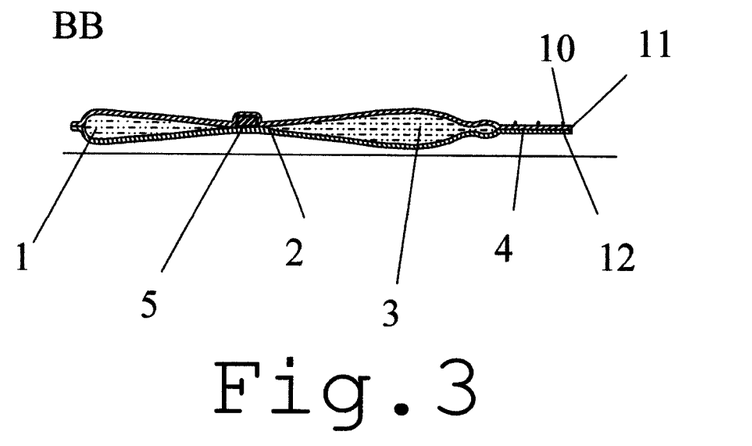
FIG. 3 is a cross section BB.

FIG. 3 shows a cross section BB through the first embodiment fluid filled insole. Rear reservoir 1 and front reservoir 3 are filled with a heavy and viscous fluid that flows through passageways 2, 2a and 2b. The magnet 5 is disposed in the midfoot region between rear reservoir 1 and front reservoir 3. The magnet 5 may not be in contact with the heavy and viscous fluid. The fluid used is a thick or heavy liquid that is resistant to flow, but not so thick that flow is unduly restricted. The density of said fluid, measured by g/cm3, is higher than the density of water (density=weight) and thus, a higher weight than water. As a result of the higher weight of the fluid (compared to water), the rate of flow of the fluid is restricted which in turn allows the fluid to function as a means of flow restriction. Said means of flow restriction enable an improved weight pressure distribution across the plantar surface of the user's foot. The distal front foot 4 may not contain any fluid and comprises a upper layer 11 and lower layer 12.

Figure 1:
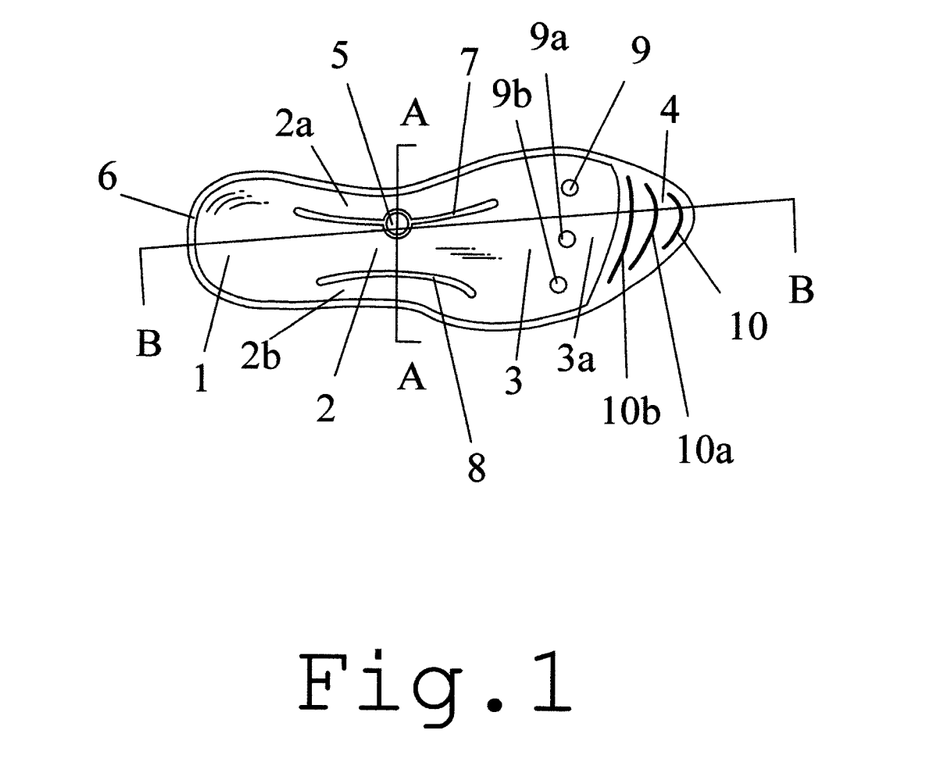
FIG. 1 is a top view of the shoe insole.

FIGS. 1 and 3 show at least three indicators arranged following the curvature of distal front foot 4. Three indicators are shown where the most distal indicator is numbered 10, the most proximal indicator is numbered 10b and the indicator in between indicators 10 and 10b is numbered 10a. Said indicators 10, 10a and 10b are not in contact with the heavy and viscous fluid. Indicators 10, 10a and 10b allow the user to trim the fluid filled insole to customize sizing and/or fit.

Figure 4:
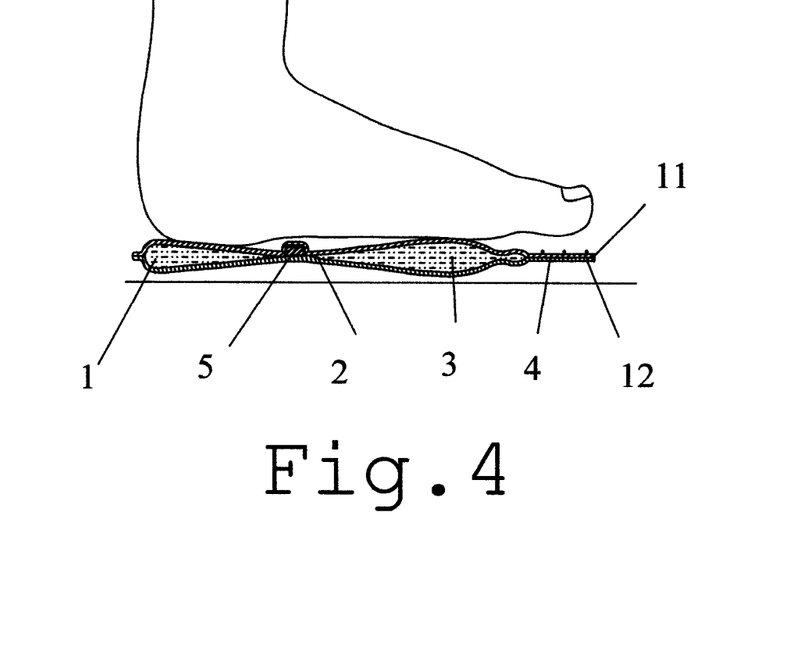
FIG. 4 is a cross section with a user's foot standing on the insole.

FIG. 4 illustrates the cross section BB with a user's foot standing on the fluid filled insole. It is intended for a user's foot to be in contact with the upper layer 11. It is intended for the heel region of a user's foot to step onto mainly rear reservoir 1. It is intended for the arch region of a user's foot to step onto the passageways 2, 2a and 2b. The magnet 5 is intended to be under the user's arch. It is intended for the region of the user's foot comprising the balls of the foot to step onto the front reservoir 3. It is intended for the toe region of the user's foot is rest atop the distal front foot 4.

With the insole comprising of a rear reservoir 1, control means 2, 2a, and 2b, and front reservoir 3, a hydraulic system exists in place. Liquids are virtually incompressible, much like solid particles. For example, when jumping into a swimming pool, it is important to dive correctly into the water. Jumping into the pool of water with a large surface area (such as the stomach facing downward) hurts much more than jumping into the pool of water in a streamlined manner due to the inability of the liquid to be compressed. As a result of this characteristic in which the liquid is incompressible, the pressure must stay constant all the way through ft, even when you're pushing it hard at one end or the other. Pressure is defined as the force acting per unit of area. The external force that activates this hydraulic system is the movement and distribution of the user's weight on top of the insole due to natural movement, such as walking. As the user moves, they will exert an amount of force on either rear reservoir 1 or front reservoir 3 pushing the heavy viscous fluid through passageways 2, 2a, and 2b. With the narrowing passageways 2, 2a, and 2b disposed between reservoirs 1 and 3, the pressure of the liquid within the insole that is intended for the user's foot arch is increased. The heavy viscous fluid within the insole also works to increase this pressure as well by decreasing flow rate, keeping the fluid within the passageways 2, 2a, and 2b for a longer period of time compared to water. Acting together, this increase in pressure may generate greater arch support for the user's foot.

Figure 5:
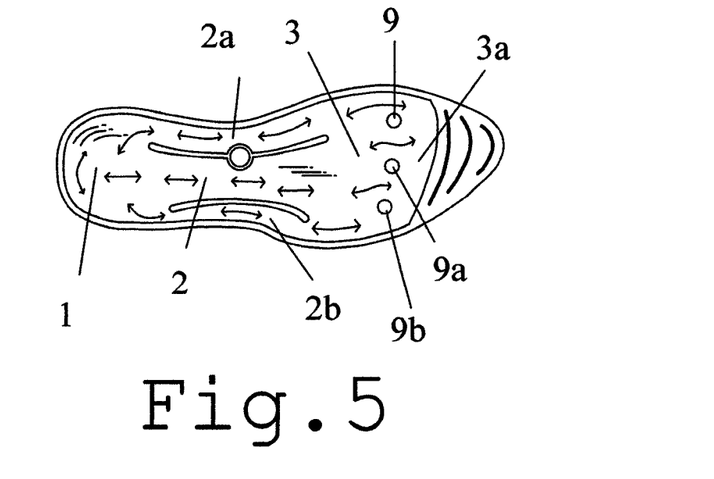
FIG. 5 is an illustration of the flow of the fluid inside the insole.

FIG. 5 is an illustration of the flow of the heavy and viscous fluid inside the insole. Said fluid may flow between rear reservoir 1 and front reservoir 3. The heavy and viscous fluid passes through passageways 2, 2a and 2b. As a result of the welded seams 9, 9a and 9b located within the front reservoir 3, there is a divided region distal to the front reservoir 3 numbered 3a. The welded seams 7, 8, 9, 9a, and 9b work together in conjunction with the heavy and viscous fluid as means for flow restriction between rear reservoir 1 and front reservoir 3, and areas numbered 3 and 3a. The weight of the user pressurizes the fluid within the said reservoirs. The pressurized fluid will constantly move the non-loaded parts of the insole upwards. Movement or weight shifts by the user will cause fluid movement, whereby a constant movement of the small internal foot muscles occurs. The movement of the liquid will result in the user's body weight being distributed more evenly over the area of the foot; thus relieving peak pressures of the foot muscles. A constant massage of the foot sole occurs for each time weight distribution is changed by the movement of the fluid within the reservoirs.

The user may also experience an improvement in balance. Balance is defined as a physical equilibrium that stems from an even distribution of the body's weight leading to stability. Balance is an underrated principle of our everyday functioning. It keeps you upright, allows for walking without assistance and helps prevent injury. As we age, balance becomes more of an issue as our bodily systems weaken. Disequilibrium (a loss of balance) is the uneven distribution of the body's weight that may lead to muscle weakness and unstable joints. With the fluid filled insole, the heavy and viscous fluid may be able to compensate for the uneven distributions that may lead to disequilibrium (a loss of balance). The viscous fluid within the insole is dynamic and movement or weight shifts by the user will cause fluid movement. The movement of the liquid will result in the user's body weight being distributed more evenly over the area of the foot, which may establish an improvement of balance.

The user may also experience a decrease in joint pains as a result of the shock absorption provided by the fluid-filled insole. Each walking step creates an impact on the user's joints such as the ankles and knees. Especially during movements of running or jogging, the impact on said joints are greatest and may lead to joint pains. Natural running form occurs as one foot pushes the whole body forward followed by the other foot landing in front of the body and this set of movements is repeated. Between one foot pushing on the ground and the other foot landing down, the whole of the user's body is mid-air where no part of the body is touching the ground. Thus, when the landing foot touches the ground, the force of the impact may be great enough to cause stress on joints such as the ankles and knees. With the fluid-filled insole, the heavy and viscous fluid may absorb a portion of this force from the impact between the foot and the ground. This cushioning effect is a result of the density of the fluid within the insole, allowing for the liquid to disperse slowly even after impact. The layer of heavy and viscous fluid may allow the user to experience less of an impact and therefore the user may experience less joint pains.

Figure 6:
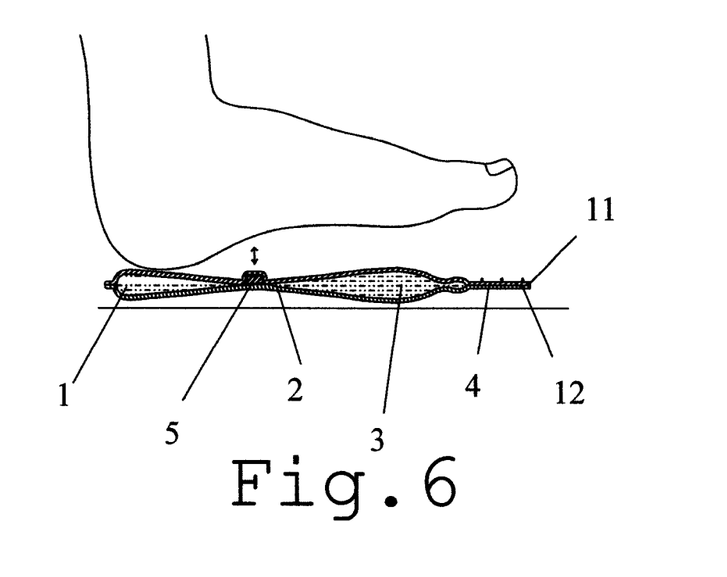
FIG. 6 is an illustration of the pump action starting with the heel stepping on the rear reservoir.
Figure 7:
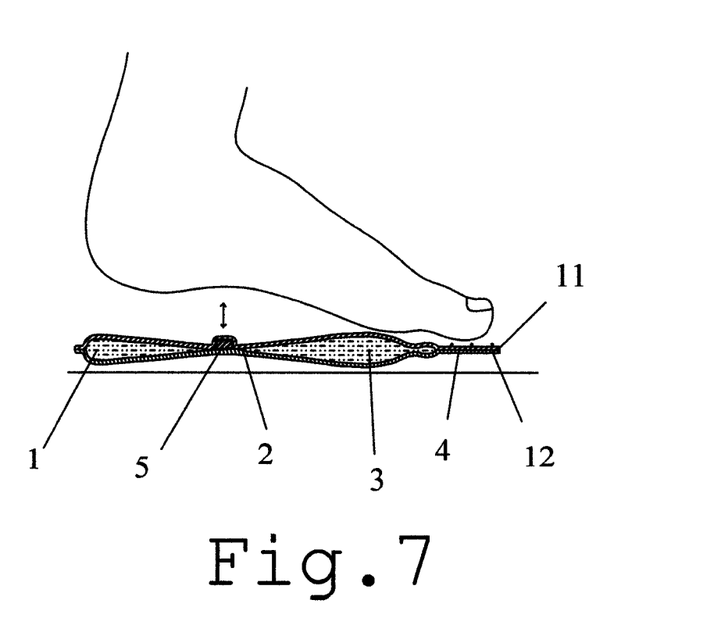
FIG. 7 is an illustration of the ball of the foot stepping on the front reservoir.

FIGS. 6 and 7 illustrate the pump action that occurs when the user steps on the reservoirs within the insole. Together, FIGS. 6 and 7 illustrate a user's natural foot movement when walking in which each foot touches the ground in a heel-toe-heel-toe manner. Each time the user's weight distribution is modified, as with walking or any other means of bodily movement, the insole provides a massaging action due to the flow of the heavy and viscous fluid and the upward and downward movement of the magnet 5. The magnet 5 may be in contact with the user's foot arch area providing a kneading action for the foot sole simulating a physical massage. Together, the massaging flow of the heavy and viscous fluid combined with the upward and downward movement of the magnet 5 allows for an added effectiveness for a massaging action.

FIG. 6 illustrates the heel region of the user's foot stepping onto the rear reservoir 1. With this action, the region of the ball of the foot may not be in contact with the front reservoir 3. The heavy and viscous fluid inside rear reservoir 1 is thus pressurized to flow towards front reservoir 3 passing through passageways 2, 2a and 2b. As the pressurized fluid is pushed between reservoirs, the magnet 5 moves upward and downward beneath the user's foot arch.

FIG. 7 illustrates the ball of the user's foot stepping onto the front reservoir 3. With this action, the heel region of the user's foot may not be in contact with the rear reservoir 1. The heavy and viscous fluid in the front reservoir 3 is pressurized with this action and thus flows towards the rear reservoir 1 by means of passageways 2, 2a and 2b. As the pressurized fluid is pushed between reservoirs, the magnet 5 moves upward and downward beneath the user's foot arch.

The magnet 5 provides both benefits of physical stimulation simulating massage kneading and magnetotherapy. Magnetotherapy uses magnetic fields to provide therapeutic and restorative treatments to limbs, organs, and other parts of the body. Generally, one means by which magnetotherapy may be achieved is by bringing a magnet into close proximity to an affected body part. This is achieved through the insole as the user's weight distribution is modified, as with walking or any other means of bodily movement, bringing the magnet 5 in close proximity of the user's foot. Charged particles, such as ions and electrolytes, experience a force acting on them when they move through a magnetic field. Ions and electrolytes and the like, as charged particles, exist within human blood, which will experience a force when exposed to a magnetic field. When experiencing a force, the charged particles within human blood may move and generate heat causing the associated blood vessels to widen. The widening of the blood vessel would then allow increased volumes of blood to flow through the blood vessel. The heat that may be generated acts as a stimulus. The increase in blood circulation/flow allows for the improvement of the transport of oxygen and nutrients to the cells in the foot and the removal of waste products excreted from the cells. Thus there may be further relief from foot pain, hard skin and in extreme situations, ulceration.

The sole of the foot is known for its sensitivity and for the fact that several nerve endings terminate in the sole of the foot. In some schools of medicinal thought, the sole of the foot provides therapeutic access to other parts of the body due to the connection of the nerves in the foot with such other areas. For example, in Chinese and other Oriental forms of medicine, different areas of the foot may correspond to different areas of the body. Affecting one part of the person's foot thereby may influence the biological or biochemical activities in other areas of the body. As is known with acupuncture, the stimulation or engagement of nerves, plexus, or the like by long, thin needles may serve to affect other areas of the body. The same may be similarly true with magnetotherapeutic devices when applied to various areas. In this way, the fluid filled insole may provide the user with magnetotherapy.

Figure 8:
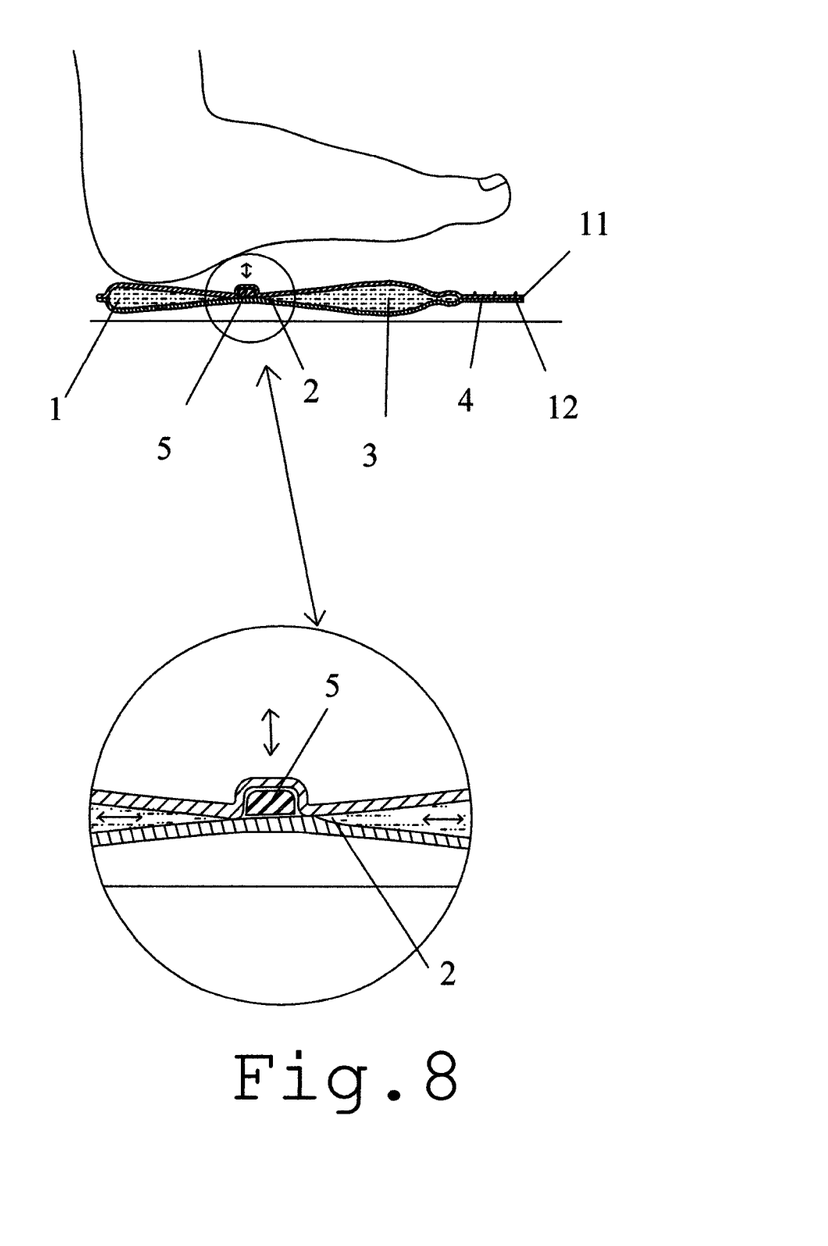
FIG. 8 is an enlargement of the magnet.

FIG. 8 shows an enlargement of the magnet 5 through cross section BB. The magnet 5 is disposed along welded seam 7 and between medial passageway 2a and passageway 2. The magnet 5 moves upward and downward in place as the fluid passes between reservoirs 1 and 3 through passageways 2, 2a and 2b to provide a massaging action. The magnet 5 may not be in contact with the heavy and viscous fluid found within the reservoirs.

Figure 9:
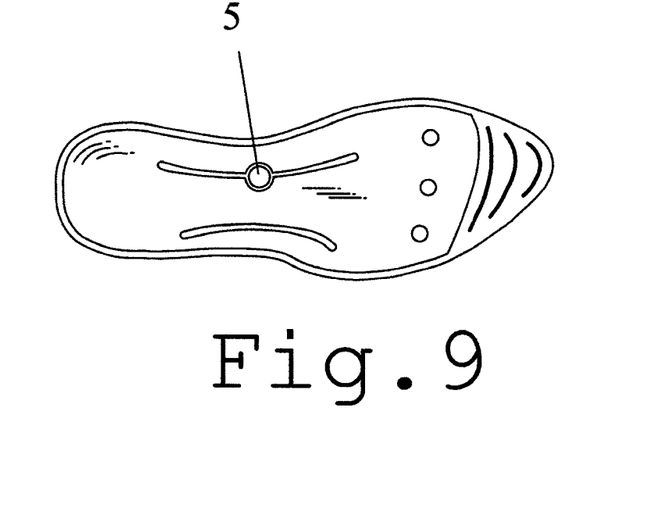
FIG. 9 is the first embodiment of the insole.

FIG. 9 shows the first embodiment of the fluid filled insole with magnet 5.

Figure 10:
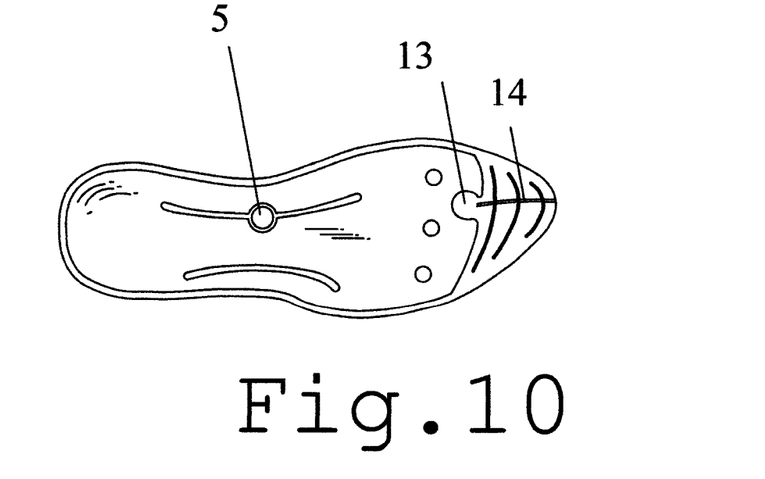
FIG. 10 is a second embodiment of the insole.

FIG. 10 shows a second embodiment of the fluid filled insole with magnet 5. An indentation 13 extends towards front reservoir 3 that is not filled with fluid. Indicator 14 may run along the length of distal front foot 4 and end inside indentation 13. Indicator 14 and indentation 13 allow for the user to modify the insole to wear with footwear designed as sandals and the like without compromising the benefits of the fluid filled reservoirs 1 and 3.

Figure 11:
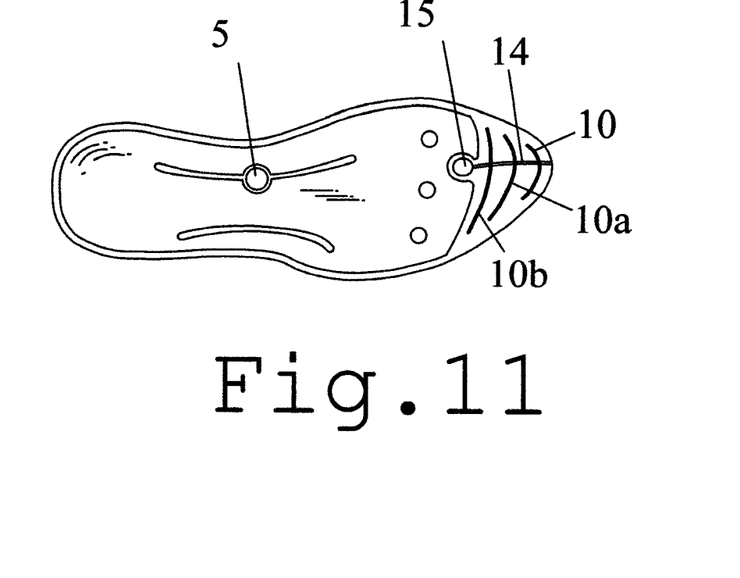
FIG. 11 is a third embodiment of the insole.

FIG. 11 shows a third embodiment of the fluid filled insole with magnet 5. An additional indicator 14 is perpendicular to the indicators 10, 10a and 10b. Said indicator 14 may run along the length of distal front foot 4 as part of the upper layer 11. Indicator 14 may be modified in a similar manner as indicators 10, 10a and 10b for customization for sizing and/or fit. Within indentation 13 may comprise a pre-cut hole 15. Pre-cut hole 15 is a hole that passes through upper layer 11 and lower layer 12. Indicator 14 and pre-cut hole 15 allow for the user to wear the insole with footwear designed as sandals and the like.

Figure 12:
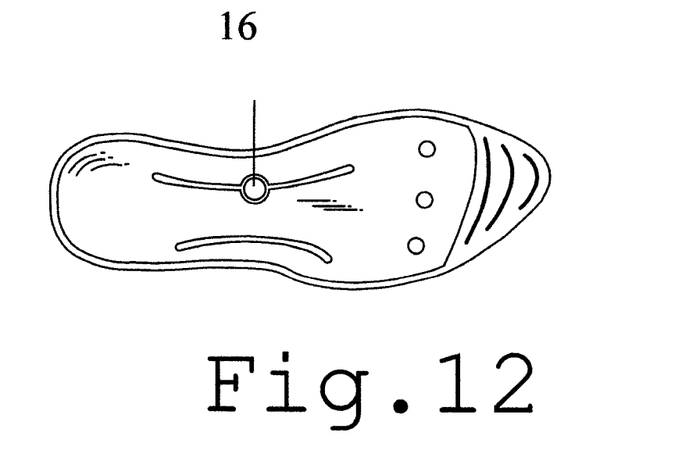
FIG. 12 is a fourth embodiment of the insole.

FIG. 12 shows a fourth embodiment of the fluid filled insole. A disc 16 is disposed in the midfoot region between rear reservoir 1 and front reservoir 3. The disc 16 may not be in contact with the heavy and viscous fluid. A disc 16 is sandwiched between upper layer 11 and lower layer 12. The disc 16 is disposed along welded seam 7 and between medial passageway 2a and central passageway 2.

The disc 16 provides the benefits of physical stimulation simulating massage kneading. With the massaging action, the disc 16 may aid in comfort by increasing blood circulation to the foot.

Figure 13:
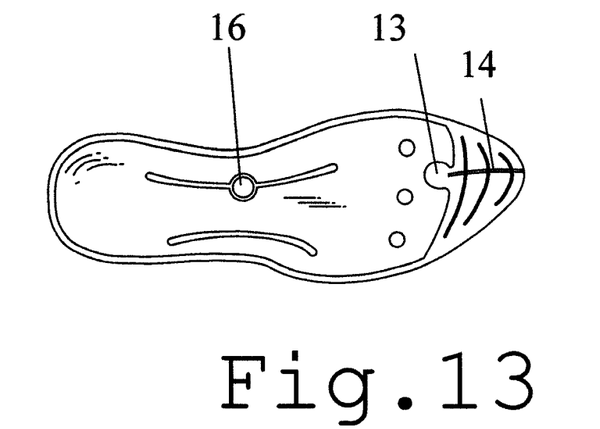
FIG. 13 is a fifth embodiment of the insole.

FIG. 13 shows a fifth embodiment of the fluid filled insole. In addition to the disc 16, an indentation 13 extends towards front reservoir 3 that is not filled with fluid. Indicator 14 may run along the length of distal front foot 4 and end inside indentation 13. Indicator 14 and indentation 13 allow for the user to modify the insole to wear with footwear designed as sandals and the like.

Figure 14:
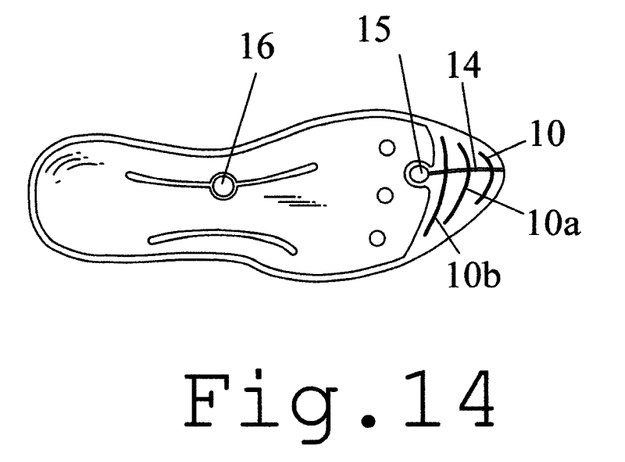
FIG. 14 is a sixth embodiment of the insole.

FIG. 14 shows a sixth embodiment of the fluid filled insole. In addition to the disc 16, an additional indicator 14 is perpendicular to the indicators 10, 10a and 10b. Said indicator 14 may run along the length of distal front foot 4 as part of the upper layer 11. Indicator 14 may be modified in a similar manner as indicators 10, 10a and 10b for customization for sizing and/or fit. Within indentation 13 may comprise a pre-cut hole 15. Pre-cut hole 15 is a hole that passes through upper layer 11 and lower layer 12. Indicator 14 and pre-cut hole 15 allow for the user to wear the insole with footwear designed as sandals and the like.

The features that distinguish the current invention from the prior art is further the magnet and the minimized number of parts needed to manufacture the insole. With the added magnet, the insole will be able to provide the user with benefits associated with magnetotherapy. The minimized number of parts required to manufacture the insole allow for a cheaper cost of production while still achieving a proper hydraulic system. While various embodiments have been described, the description is intended to be exemplary, rather than limiting and it will be apparent to those of ordinary skill in the art that many more embodiments and implementations are possible. Accordingly, the embodiments are not to be restricted except in light of the attached claims and their equivalents. Also, various modifications and changes may be made within the scope of the attached claims.

What is claimed is:

1. A flexible insole for providing improved balance, physical massaging motions and cushioning; the insole comprising a fluid tight bladder formed by a flexible top foil and a flexible bottom foil which are welded together about an outer periphery of the top foil and the bottom foil, the fluid tight bladder comprising two fluid filled reservoirs, wherein the two fluid reservoirs are in fluid communication with each other and wherein the fluid reservoirs contain a heavy and viscous fluid, wherein the fluid filled bladder comprises at least one weld seams within the bladder to control the fluid within, and a permanent magnet is disposed within the at least one weld seams so as to not be in contact with the fluid.

2. The flexible insole according to claim 1, wherein the two fluid-filled reservoirs comprises a number of channels creating a hydraulic system when a user experiences a shift in weight.

3. The flexible insole according to claim 1, wherein the permanent magnet is made of a hard material to provide physical massaging motions.

\* \* \* \* \*